United States Patent [19]
Wiechert et al.

[11] 4,129,564
[45] Dec. 12, 1978

[54] SPIROLACTONES

[75] Inventors: Rudolf Wiechert; Dieter Bittler; Ulrich Kerb; Jorge Casals-Stenzel; Wolfgang Losert, all of Berlin, Fed. Rep. of Germany

[73] Assignee: Schering, A.G. Patentabteilung, Berlin, Fed. Rep. of Germany

[21] Appl. No.: 850,524

[22] Filed: Nov. 11, 1977

[30] Foreign Application Priority Data

Nov. 16, 1976 [DE] Fed. Rep. of Germany ....... 2652761

[51] Int. Cl.² .......................... A61K 31/58; C07J 1/00
[52] U.S. Cl. ................................ 260/239.57; 424/241
[58] Field of Search ................................... 260/239.57; /Machine Searched Steroids

[56] References Cited
U.S. PATENT DOCUMENTS 3,257,390  6/1966  Patchett .......................... 260/239.55
3,900,467  8/1975  Irmscher et al. ................. 260/239.57

Primary Examiner—Elbert L. Roberts
Attorney, Agent, or Firm—Millen & White

[57] ABSTRACT

New spirolactones of the formula

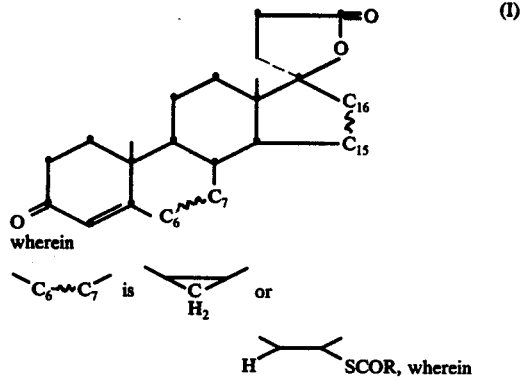

wherein

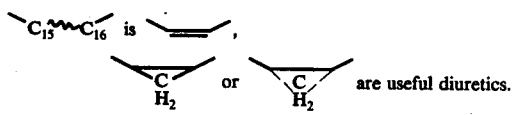

R is a lower alkyl of up to 5 carbon atoms, and $\overset{\frown}{C_{15}\!\sim\!\!\sim\!\! C_{16}}$ is 〰️, ⌄C⌄/H₂ or ⌄C⌄/H₂ are useful diuretics.

19 Claims, No Drawings

SPIROLACTONES

SUMMARY OF THE INVENTION

The present invention provides novel spirolactones of Formula I

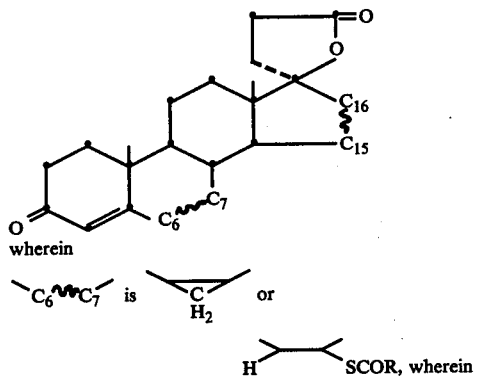

wherein

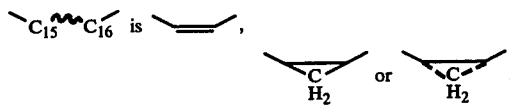

R is a lower alkyl of up to 5 carbon atoms, and

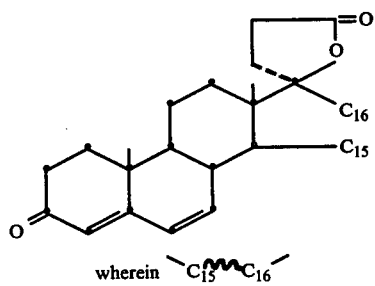

Lower alkyl residues include branched and unbranched groups, preferably methyl, ethyl and n-propyl.

DETAILED DISCUSSION

The spirolactones of Formula I can be prepared by conventionally introducing the methylene group or the thiacyl group into the $\Delta^6$-unsaturated spirolactones of Formula II (II)

is as defined above.

The methylene group is introduced into the compounds of Formula II in accordance with conventional methods, for example, by reaction of the compounds with dimethyl sulfoxonium methylide in an aprotic solvent, such as dimethyl sulfoxide, dimethylformamide, dioxane, or a mixture of dimethyl sulfoxide and tetrahydrofuran. See for reference, E. J. Corey and M. Chaykovsky, J. Am. Chem. Soc. 84 (1962)867 and ibid. 84 (1962)3782.

This process is advantageously conducted at 20°–40° C. under a protective gas atmosphere, such as nitrogen.

The dimethyl sulfoxonium methylide is suitably prepared by reaction of trimethyl sulfoxonium iodide or chloride with a base, such as sodium hydride, sodium hydroxide, potassium tert-butylate, or sodium methylate.

The dimethyl sulfoxonium methylide is prepared in a conventional manner (see for reference, L. F. Fieser & M. Fieser, Reagents for Organic Synthesis, J. Wiley & Sons, Inc., N.Y., 1967, p. 315).

The thiacyl group is also introduced into the compounds of Formula II in accordance with known procedures. Especially suitable is the reaction of the compounds with the corresponding thio acid in the presence of a protonic solvent, such as methanol or ethanol, optionally in a mixture thereof with water, while heating. For reference, see process described in U.S. Pat. No. 3,013,102.

The preferred temperature range is that from above room temperature up to the boiling point of the reaction mixture.

It is also possible to conduct the thiacylation without a solvent.

The three starting materials of Formula II which are required for preparation of all compounds of Formula I in accordance with the foregoing procedures, i.e.,

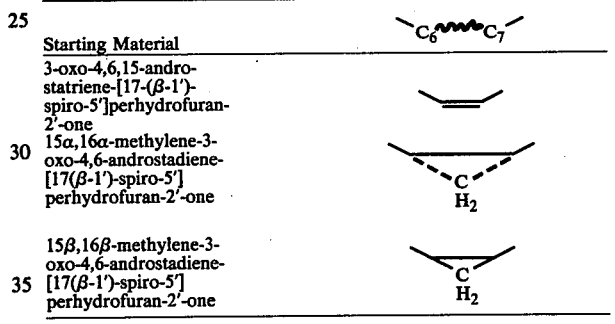

can be prepared as follows:

3-oxo-4,6,15-androstatriene-[17-($\beta$-1')-spiro-5']perhydrofuran-2'-one 20.0 g. of 3$\beta$-hydroxy-5,15-androstadien-17-one is combined in 280 ml. of absolute tetrahydrofuran with 4.34 g. of freshly pressed lithium wire. Then, 36 ml. of 1-bromo-3-dimethoxypropane is added dropwise under ice cooling within 30 minutes. After 1.5 hours of agitation at ice-bath temperature, the mixture is filtered off from the unreacted lithium, and the filtrate is stirred into ice water. The precipitate is filtered off, washed with water, and taken up in methylene chloride.

After drying and evaporation, the residue is chromatographed on silica gel, thus obtaining 19.9 g. of 17$\alpha$-(3'-dimethoxypropyl)-5,15-androstadiene-3$\beta$,17$\beta$-diol in the form of an oil.

19.9 g. of 17$\alpha$-(3'-dimethoxypropyl)-5,15-androstadiene-3$\beta$,17$\beta$-diol is combined in 500 ml.of acetone under ice cooling with 1.0 g. of p-toluenesulfonic acid and stirred for 15 minutes under cooling. The mixture is then introduced under agitation into ice water which contains sodium bicarbonate; the precipitate is filtered off, washed, and taken up in methylene chloride. After drying and evaporation, 9.2 g. of crude 3$\beta$-hydroxy-5,15-androstadiene-[17($\beta$-1')-spiro-5']perhydrofuran-2'$\xi$-methyl ether is obtained in the form of an oil.

19.2 g. of 3$\beta$-hydroxy-5,15-androstadiene-[17($\beta$-1')-spiro-5']perhydrofuran-2'$\xi$-methyl ether is combined in 394 ml. of absolute toluene and 39.4 ml. of cyclohexanone with 3.94 g. of aluminum isopropylate in 40 ml. of absolute toluene and heated for 45 minutes under gradual distillation. The mixture is then diluted with methylene chloride, washed with dilute sulfuric acid and water, dried, and evaporated. The residue is chromatographed on silica gel, thus obtaining 17.5 g. of 3-oxo-4,15-androstadiene-[17(β-1')-spiro-5']perhydrofuran-2'ξ-methyl ether in the form of an oil.

UV: $\epsilon_{239} = 16,200$.

17.5 g. of 3-oxo-4,15-androstadiene-[17(β-1')-spiro-5']perhydrofuran-2'ξ-methyl ether is combined in 350 ml. of acetone under ice cooling with 35 ml. of chromosulfuric acid (prepared from 267 g. of CrO$_3$, 400 ml. of water, and 230 ml. of concentrated sulfuric acid, replenished with water to obtain 1 liter); the mixture is stirred for 30 minutes under cooling in an ice bath. The mixture is then stirred into ice water, the precipitate is filtered off, washed with water, and taken up in methylene chloride. After drying and evaporation; the residue is chromatographed on silica gel, thus obtaining 11.8 g. of 3-oxo-4,15-androstadiene-[17(β-1')-spiro-5']perhydrofuran-2'-one. A sample recrystallized from diisopropyl ether/acetone melts at 189.5°–191.5° C.

UV: $\epsilon_{240} = 17,300$.

10.0 g. of 3-oxo-4,15-androstadiene-[17(β-1')-spiro-5']perhydrofuran-2'-one is combined in 100 ml. of absolute dioxane with 10 ml. of triethyl orthoformate and 10 ml. of dioxane/concentrated sulfuric acid (produced from 13.5 ml. of absolute dioxane and 0.48 ml. of concentrated sulfuric acid). The mixture is stirred for 30 minutes at room temperature, combined with 2 ml. of pyridine, and diluted with ether. The ether phase is washed with water, dried, and evaporated. The residue is triturated with pyridine-containing methanol, the thus-separated crystals are vacuum-filtered. Yield: 8.9 g. of 3-ethoxy-3,5,15-androstatriene-[17(β-1')-spiro-5']perhydrofuran-2'-one, m.p. 153.5°–159° C.

UV: $\epsilon_{240} = 19,800$.

8.9 g. of 3-ethoxy-3,5,15-androstatriene-[17(β-1')-spiro-5']-perhydrofuran-2'-one is dissolved in 201 ml. of acetone, cooled in an ice bath, and combined with 1.38 ml. of pyridine, 6.36 g. of sodium acetate, and 63.6 ml. of water. Then, 4.72 g. of N-bromosuccinimide is added thereto, and 6.36 ml. of acetic acid is added dropwise over a period of 15 minutes. The mixture is further stirred for 45 minutes under ice cooling, diluted with ether, and washed neutral with water. After drying and evaporation, 10.35 g. of 6β-bromo-3-oxo-4,15-androstadiene-[17(β-1')-spiro-5']perhydrofuran-2'-one is obtained in the form of an oil.

UV: $\epsilon_{245} = 12,700$.

10.35 g. of 6β-bromo-3-oxo-4,15-androstadiene-[17(β-1')-spiro-5']perhydrofuran-2'-one is stirred in 103.5 ml. of dimethylformamide with 4.67 g. of lithium carbonate and 5.37 g. of lithium bromide for 18 hours at 100° C. The mixture is then introduced into ice water under agitation, the precipitate is filtered off, washed with water, and taken up in methylene chloride. After drying and evaporation, the residue is chromatographed. After recrystallization from diisopropyl ether/acetone, 6.5 g. of 3-oxo-4,6,15-androstatriene-[17(β-1')-spiro-5']perhydrofuran-2'-one is obtained, m.p. 182.5°–184.5° C.

UV: $\epsilon_{284} = 27,100$.

15α,16α-methylene-3-oxo-4,6-androstadiene-[17(β-1')-spiro-5']perhydrofuran-2'-one 15 g. of 3β-hydroxy-15α,16α-methylene-5-androsten-17-one (produced, for example, according to DOS [German Unexamined Laid-Open Application] 2,109,555) is combined in 150 ml. of absolute tetrahydrofuran under ice cooling with 3.6 g. of lithium and thereafter 30 ml. of 1-bromo-3-dimethoxypropane is added dropwise within 30 minutes. After agitation for 2.5 hours at ice bath temperature, the mixture is separated from the unreacted lithium, and the filtrate is stirred into ice water. The thus-obtained precipitate is filtered off, washed with water, and taken up in methylene chloride. After drying and evaporation, the residue is chromatographed on silica gel, thus obtaining 16.8 g. of 17α-(3'-dimethoxypropyl)-15α,16α-methylene-5-androstene-3β,17β-diol. A sample recrystallized from diisopropyl ether/acetone melts at 153°–159° C.

16.5 g. of 17α-(3'-dimethoxypropyl)-15α,16α-methylene-5-androstene-3β,17β-diol is agitated in 410 ml. of 70% acetic acid for 18 hours at room temperature. The mixture is then stirred into ice water, and the thus-obtained precipitate filtered off, taken up in chloroform, and washed with sodium bicarbonate solution and water. After drying and evaporation, the residue is chromatographed on silica gel, thus obtaining 11.5 g. of 3β-hydroxy-15α,16α-methylene-5-androstene-[17(β-1')-spiro-5']perhydrofuran-2'ξ-ol. A sample recrystallized from diisopropyl ether/acetone melts at 194°–202° C.

10.5 g. of 3β-hydroxy-15α,16α-methylene-5-androstene-[17(β-1')-spiro-5']perhydrofuran-2'ξ-ol is combined in 210 ml. of absolute toluene with 21 ml. of cyclohexanone and 2.1 g. of aluminum isopropylate in 20 ml. of absolute toluene, and then heated for 45 minutes under gradual distillation. The mixture is then diluted with methylene chloride, washed with 2N sulfuric acid and water, dried, and evaporated. Yield: 11.5 g. of crude 15α,16α-methylene-3-oxo-4-androstene-[17(β-1')-spiro-5']perhydrofuran-2'!-ol as an oil. A sample purified by preparative layer chromatography and recrystallization from diisopropyl ether/acetone melts at 259°–268° C.

UV: $\epsilon_{241} = 16,500$.

10.5 g. of 15α,16α-methylene-3-oxo-4-androstene-[17(β-1')-spiro-5']perhydrofuran-2'ξ-ol is combined in 100 ml. of acetone under ice cooling with 10 ml. of chromosulfuric acid (prepared from 267 g. of CrO$_3$, 400 ml. of water, and 230 ml. of concentrated sulfuric acid, replenished to a volume of 1 liter with water). The mixture is agitated for 1 hour, then stirred into ice water, washed with water, and taken up in methylene chloride. After drying and evaporation, the residue is chromatographed on silica gel, thus obtaining 8.2 g. of 15α,16α-methylene-3-oxo-4-androstene-[17(β-1')-spiro-5']perhydrofuran-2'-one. A sample recrystallized from diisopropyl ether/acetone melts at 180°–181° C.

UV: $\epsilon_{240} = 16,600$.

7.2 g. of 15α,16α-methylene-3-oxo-4-androstene-[17(β-1')-spiro-5']perhydrofuran-2'-one is combined in 72 ml. of absolute dioxane and 7.2 ml. of triethyl orthoformate with a solution of 7.2 ml. of absolute dioxane and 0.26 ml. of concentrated sulfuric acid. The mixture is stirred for 30 minutes at room temperature. Then, 2 ml. of pyridine is added thereto, the mixture is diluted with ether, washed with water, and dried. After evaporation, 8.5 g. of crude 3-ethoxy-15α,16α-methylene-3,5-androstadiene-[17(β-1')-spiro-5']perhydrofuran-2'-one is obtained.

UV: $\epsilon_{241} = 15{,}700$.

8.5 g. of 3-ethoxy-15α,16α-methylene-3,5-androstadiene-[17(β-1')-spiro-5']perhydrofuran-2'-one is dissolved in 192 ml. of acetone, cooled in an ice bath, and combined with 1.32 ml. of pyridine, 6.08 g. of sodium acetate, and 60.8 ml. of water; then, 4.51 g. of N-bromosuccinimide is added thereto and within 10 minutes, 6.08 ml. of acetic acid is added dropwise to the reaction mixture. The mixture is further stirred for 1 hour at ice bath temperature, diluted with ether, washed with water, and dried. After evaporation, 9.6 g. of crude 6β-bromo-3-oxo-4-androstene-[17(β-1')-spiro-5']perhydrofuran-2'-one is obtained.

9.6 g. of 6β-bromo-3-oxo-4-androstene-[17(β-1')spiro-5']perhydrofuran-2'-one is stirred in 96 ml. of dimethylformamide with 3.75 g. of lithium carbonate and 4.4 g. of lithium bromide for 18 hours at 100° C. The mixture is then stirred into ice water, the thus-obtained precipitate is filtered off, taken up in methylene chloride, washed with 2N sulfuric acid and water, and dried. After evaporation, the residue is chromatographed on silica gel, thus obtaining 6.5 g. of 15α,16α-methylene-3-oxo-4,6-androstadiene-[17(β-1')-spiro-5']-perhydrofuran-2'-one. A sample recrystallized from diisopropyl ether melts at 180.5°–182.5° C.

UV: $\epsilon_{283} = 26{,}300$.

15β,16β-methylene-3-oxo-4,6-androstadiene-[17(β-1')-spiro-5']perhydrofuran-2'-one 15 g. of 3β-hydroxy-15β,16β-methylene-5-androsten-17-one (produced, for example, according to German Pat. No. 1,593,500) is reacted in 150 ml. of absolute tetrahydrofuran with 3.27 g. of lithium and 29 ml. of 1-bromo-3-dimethoxypropane for 2 hours at ice bath temperature and for 4 hours at room temperature. The mixture is filtered off from the unreacted lithium, the filtrate is stirred into ice water, the precipitate is filtered off and taken up in methylene chloride. After drying and evaporation, the residue is chromatographed on silica gel. Yield: 17.4 g. of 17α-(3'-dimethoxypropyl)-15β,16β-methylene-5-androstene-3β,17β-diol.

17.0 g. of 17α-(3'-dimethoxypropyl)-15β,16β-methylene-5-androstene-3β,17β-diol is agitated in 340 ml. of 70% acetic acid for 18 hours at room temperature. The mixture is then stirred into ice water; the thus-obtained precipitate is filtered off and taken up in methylene chloride. The methylene chloride phase is washed with sodium bicarbonate solution and water, dried, and evaporated, thus obtaining 13.8 g. of 3β-hydroxy-15β,16β-methylene-5-androstene-[17(β-1')-spiro-5']-perhydrofuran-2'-ol as a crude product.

8.8 g. of 3β-hydroxy-15β,16β-methylene-5-androstene[17(β-1')-spiro-5']perhydrofuran-2'ξ-ol is combined in 176 ml. of absolute toluene and 17.6 ml. of cyclohexanone with 1.76 g. of aluminum isopropylate in 50 ml. of absolute toluene and heated for 3 hours under gradual distillation. The mixture is then diluted with ether, washed with 2N sulfuric acid and water, dried, and evaporated. The residue is chromatographed on silica gel, thus obtaining 4.3 g. of 15β,16β-methylene-3-oxo-4-androstene-[17(β-1')-spiro-5']perhydrofuran-2'-one. A sample recrystallized from diisopropyl ether/acetone melts at 178.5°–179.5° C.

UV: $\epsilon_{241} = 16{,}500$.

4.2 g. of 15β,16β-methylene-3-oxo-4-androstene-[17(β-1')-spiro-5']perhydrofuran-2'-one is refluxed in 84 ml. of tert.-butanol with 4.2 g. of chloranil for 18 hours. The solvent is distilled off under vacuum, and the residue is chromatographed on silica gel. For purposes of additional purification, preparative layer chromatography is employed. Yield: 1.1 g. of 15β,16β-methylene-3-oxo-4,6-androstadiene-[17(β-1')-spiro-5']perhydrofuran-2'-one as an oil.

UV: $\epsilon_{284} = 25{,}700$.

For each starting material, after the preparative reaction is terminated, the reaction mixture is worked up in a conventional fashion to obtain the desired compound, e.g., by precipitation, extraction, recrystallization, and/or chromatography.

The compounds of this invention possess valuable pharmacological properties. They are, inter alia, diuretics of the aldosterone antagonist type, i.e., they reverse the effect of desoxycorticosterone on the excretion of sodium and potassium. Unexpectedly, the compounds of this invention display superior activity in comparison with the conventional diuretic, spironolactone. This effect can be determined using the test model of Hollman (G. Hollmann et al., "Tubulaere Wirkungen und renale Elimination von Spirolactonen" (Tubular Effects and Renal Elimination of Spirolactones], NaunynSchmiedebergs Arch. Exp. Path. Pharmak. 247, 419 (1964); P. Marx, "Renal Effects of d-Aldosterone and Its Antagonist Spironolactone," dissertation of the Medical Faculty, Berlin Free University, 1966).

The compounds of Formula I can be administered to mammals, including humans, e.g., parenterally or enterally (orally) in accordance with fully conventional procedures, e.g., those used in the administration of spironolactone. Thus, suitable dosages as a diuretic are 20–500 mg/day for human patients.

The pharmacologically active compounds of Formula I can be processed in accordance with conventional methods of galenic pharmacy to produce medicinal agents, especially for oral administration. Conventional excipients include pharmaceutically acceptable organic or inorganic carrier substances suitable for parenteral, enteral or topical application which do not deleteriously react with the active compounds. Suitable pharmaceutically acceptable carriers include, but are not limited to, water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 10–100 mg in a pharmaceutically acceptable carrier per unit dosage.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

1.5 g. of 3-oxo-4,6,15-androstatriene-[17($\beta$-1')-spiro5']perhydrofuran-2'-one is refluxed in 22.5 ml. of methanol with 1.5 ml. of thioacetic acid for 2 hours. The mixture is then diluted with ether, washed with water, sodium bicarbonate solution, and water, dried, and evaporated. The residue is chromatographed on silica gel, thus obtaining 1.05 g. of 7$\alpha$-acetylthio-3-oxo-4,15-androstadiene-[17($\beta$-1')-spiro-5']perhydrofuran-2'-one, m.p. 317°–319° C. (decomposition).

UV: $\epsilon_{238}$ = 19,800.

EXAMPLE 2

1.0 g. of 3-oxo-4,6,15-androstatriene-[17($\beta$-1')-spiro-5']perhydrofuran-2'-one is refluxed in 15 ml. of methanol with 1 ml. of thiopropionic acid for 16 hours. The mixture is worked up and purified as described in Example 1, thus obtaining 670 mg. of 3-oxo-7$\alpha$-propionylthio-4,15-androstadiene-[17($\beta$-1')-spiro-5']perhydrofuran-2'-one.

UV: $\epsilon_{238}$ = 18,500.

EXAMPLE 3

4.13 g. of trimethyl sulfoxonimum iodide is agitated in 75 ml. of dimethyl sulfoxide with 512 mg. of 80% sodium hydride oil suspension for 2 hours under nitrogen. The almost clear solution is combined with 3.0 g. of 3-oxo-4,6,15-androstatriene-[17($\beta$-1')-spiro-5']perhydrofuran-2'-one and agitated for 24 hours at room temperature. The mixture is then stirred into ice water, the precipitate is filtered off, washed with water, and taken up in ether. After drying and evaporation, the residue is chromatographed on silica gel and then further purified by preparative layer chromatography, thus obtaining 520 mg. of 6$\beta$,7$\beta$-methylene-3-oxo-4,15-androstadiene-[17($\beta$-1')-spiro-5']-perhydrofuran-2'-one.

UV: $\epsilon_{266}$ = 18,100.

EXAMPLE 4

1.4 g. of 15$\alpha$,16$\alpha$-methylene-3-oxo-4,6-androstadiene-[17($\beta$-1')-spiro-5']perhydrofuran-2'-one is refluxed in 22.5 ml. of methanol with 3 ml. of thioacetic acid for 17 hours. The mixture is then diluted wit ether, washed with sodium bicarbonate solution and water, dried, and evaporated. The residue is purified by way of preparative layer chromatography and recrystallized from diisopropyl ether/acetone. Yield: 1.08 g. of 7$\alpha$-acetylthio-15$\alpha$,16$\alpha$-methylene-3-oxo-4-androstene-[17($\beta$-1')-spiro-5']perhydrofuran-2'-one, m.p. 214.5°–217.5° C.

UV: $\epsilon_{238}$ = 19,100.

EXAMPLE 5

500 mg. of 15$\alpha$,16$\alpha$-methylene-3-oxo-4,6-androstadiene-(17[$\beta$-1')-spiro-5']perhydrofuran-2'-one is refluxed in 5 ml. of methanol with 1 ml. of thiopropionic acid for 32 hours. The mixture is worked up and purified as described in Example 4. Yield: 220 mg. of 15$\alpha$,16$\alpha$-methylene-3-oxo-7$\alpha$-propionylthio-4-androstene-[17($\beta$-1')-spiro-5']perhydrofuran-2'-one.

UV: $\epsilon_{238}$ = 18,700.

EXAMPLE 6

2.75 g. of trimethyl sulfoxonium iodide is stirred in 57 ml. of dimethyl sulfoxide with 341 mg. of 80% sodium hydride oil suspension for 2 hours at room temperature. The almost clear solution is combined under nitrogen with 2.0 g. of 15$\alpha$,16$\alpha$-methylene-3-oxo-4,6-androstadiene-[17($\beta$-1')-spiro-5']perhydrofuran-2'-one and agitated for 24 hours at room temperature. The mixture is then stirred into ice water, the thus-obtained precipitate is filtered off, washed with water, and taken up in methylene chloride. After drying and evaporation, the residue is purified by repeated preparative layer chromatography, thus obtaining 520 mg. of 6$\beta$,7$\beta$,15$\alpha$,16$\alpha$-dimethylene-3-oxo-4-androstene-[17($\beta$-1')-spiro-5']perhydrofuran-2'-one.

UV: $\epsilon_{266}$ = 18,000.

EXAMPLE 7

1.0 g. of 15$\beta$,16$\beta$-methylene-3-oxo-4,6-androstadiene-[17($\beta$-1')-spiro-5']perhydrofuran-2'-one is refluxed in 15 ml. of methanol with 1 ml. of thioacetic acid for 2 hours. The mixture is then taken up in ether, washed with sodium bicarbonate solution and water, dried, and evaporated. The residue is chromatographed on silica gel. Recrystallization from diisopropyl ether/acetone yields 590 mg. of 7$\alpha$-acetylthio-15$\beta$,16$\beta$-methylene-3-oxo-4-androstene-[17($\beta$-1')-spiro-5']perhydrofuran-2'-one, m.p. 242–247° C. (decomposition).

UV: $\epsilon_{238}$ = 19,300.

EXAMPLE 8

750 mg. of 15$\beta$,16$\beta$-methylene-3-oxo-4,6-androstadiene-[17($\beta$-1')-spiro-5']perhydrofuran-2'-one is refluxed in 7.5 ml. of methanol with 0.75 ml. of thiopropionic acid for 18 hours. The mixture is worked up as described in Example 4, and the residue is purified by preparative layer chromatography, thus obtaining 320 mg. of 15β,16β-methylene-3-oxo-7α-propionylthio-4-androstene-[17(β-1')-spiro-5']perhydrofuran-2'-one as an oil.

UV: $\epsilon_{238} = 18{,}700$.

EXAMPLE 9

1.4 g. of trimethyl sulfoxonium iodide is stirred in 25 ml. of dimethyl sulfoxide with 170 mg. of 80% sodium hydride oil suspension for 1.5 hours under nitrogen. The almost clear solution is combined with 1.0 g. of 15β,16β-methylene-3-oxo-4,6-androstadiene-[17(β-1')-spiro-5']perhydrofuran-2'-one, dissolved in 10 ml. of dimethyl sulfoxide. After 24 hours of agitation at room temperature, the mixture is stirred into ice water, the precipitate is filtered off, taken up in ether, washed with water, and dried. The residue obtained after evaporation is purified by repeated preparative layer chromatography, thus producing 170 mg. of 6β,7β,15β,16β-dimethylene-3-oxo-4-androstene-[17(β-1')-spiro-5']perhydrofuran-2'-one in the form of an oil.

UV: $\epsilon_{266} = 18{,}400$.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A spirolactone of the formula

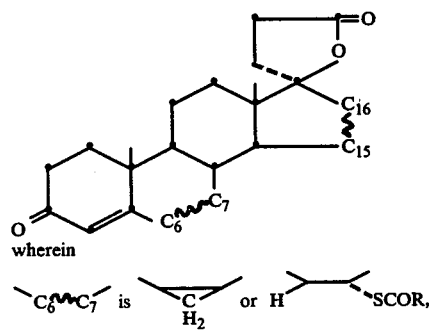

(I)

wherein

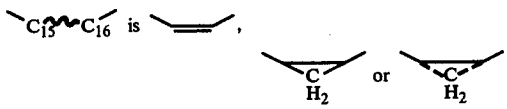

wherein R is lower alkyl of up to 5 carbon atoms, and

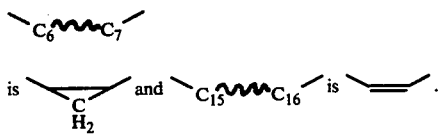

2. The spirolactone of claim 1 wherein

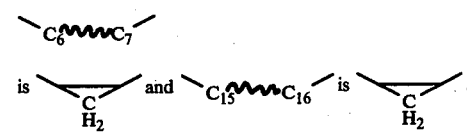

3. The spirolactone of claim 1 wherein

4. The spirolactone of claim 1 wherein

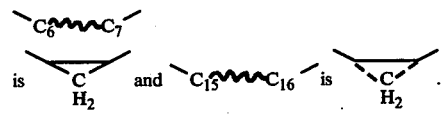

5. The spirolactone of claim 1 wherein

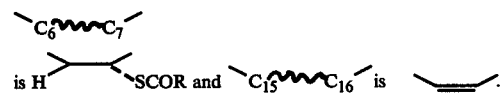

6. The spirolactone of claim 1 wherein

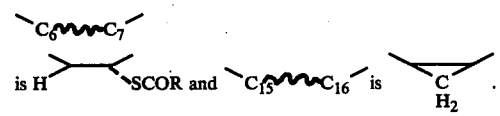

7. The spirolactone of claim 1 wherein

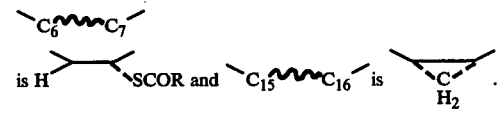

8. The spirolactone of claim 1 wherein R is methyl or ethyl.

9. 7α-Acetylthio-3-oxo-4,15-androstadiene-[17(β-1')-spiro-5']perhydrofuran-2'-one, a compound of claim 1.

10. 3-Oxo-7α-propionylthio-4,15-androstadiene-[17(β-1')-spiro-5']perhydrofuran-2'-one, a compound of claim 1.

11. 6β,7β-Methylene-3-oxo-4,15-androstadiene-[17(β-1')-spiro-5']perhydrofuran-2'-one, a compound of claim 1.

12. 15α,16α-Methylene-3-oxo-7α-propionylthio-4-androstene-[17(β-1')-spiro-5']perhydrofuran-2'-one, a compound of claim 1.

13. 6β,7β,15α,16α-Dimethylene-3-oxo-4-androstene-[17(β-1')-spiro-5']perhydrofuran-2'-one, a compound of claim 1.

14. 7α-Acetylthio-15α,16α-methylene-3-oxo-4-androstene-[17(β-1')-spiro-5']perhydrofuran-2'-one, a compound of claim 1.

15. 7α-Acetylthio-15β,16β-methylene-3-oxo-4-androstene-[17(β-1')-spiro-5']perhydrofuran-2'-one, a compound of claim 1.

16. 15β,16β-Methylene-3-oxo-7β-propionylthio-4-androstene-[17(β-1')-spiro-5']perhydrofuran-2'-one, a compound of claim 1.

17. 6β,7β,15β,16β-Dimethylene-3-oxo-4-androstene-[17(β-1')-spiro-5']perhydrofuran-2'-one, a compound of claim 1.

18. A pharmaceutical composition which comprises a diuretically effective amount of a spirolactone of claim 1 and a pharmaceutically acceptable adjuvant.

19. The method of achieving diuretic effects in mammals which comprises administering a diuretically effective amount of a spirolactone of claim 1.

* * * * *

UNITED STATES PATENT AND TRADEMARK OFFICE
CERTIFICATE OF CORRECTION

PATENT NO. : 4,129,564
DATED : December 12, 1978
INVENTOR(S) : RUDOLF WIECHERT ET AL It is certified that error appears in the above-identified patent and that said Letters Patent are hereby corrected as shown below:

Assignee: reads "Schering, A.G. Patentabteilung"

should read -- Schering Aktiengesellschaft --

Claim 16: reads " $15\beta,16\beta$-Methylene-3-oxo-7$\alpha$-propionylthio-4-androstene-[17($\beta$-1')-spiro-5']perhydrofuran-2'-one, a compound of claim 1".

should read -- $15\beta,16\beta$-Methylene-3-oxo-7$\beta$-propionylthio-4-androstene-[17($\beta$-1')-spiro-5']perhydrofuran-2'-one, a compound of claim 1 -- .

Signed and Sealed this

Fifteenth Day of May 1979

[SEAL]

Attest:

RUTH C. MASON
Attesting Officer

DONALD W. BANNER
Commissioner of Patents and Trademarks